United States Patent
Nevins

(10) Patent No.: US 7,019,464 B2
(45) Date of Patent: Mar. 28, 2006

(54) DIMMABLE FLEX ARM LAMP

(76) Inventor: Michael O. Nevins, 4880 Brooklyn Rd., Jackson, MI (US) 49201

( * ) Notice: Subject to any disclaimer, the term of this patent is extended or adjusted under 35 U.S.C. 154(b) by 3 days.

(21) Appl. No.: 10/831,113

(22) Filed: Apr. 26, 2004

(65) Prior Publication Data

US 2004/0212314 A1    Oct. 28, 2004

Related U.S. Application Data

(60) Provisional application No. 60/465,100, filed on Apr. 24, 2003.

(51) Int. Cl.
*H05B 37/02* (2006.01)
(52) U.S. Cl. .................... 315/149; 315/291; 362/108
(58) Field of Classification Search ........... 315/149, 315/224, 291, 155, DIG. 4; 36/137, 103; 362/108
See application file for complete search history.

(56) References Cited

U.S. PATENT DOCUMENTS

| | | | |
|---|---|---|---|
| 5,047,006 A | 9/1991 | Brandston et al. | 600/21 |
| 5,237,760 A * | 8/1993 | Altman et al. | 36/137 |
| 5,426,879 A | 6/1995 | Hecker | 40/427 |
| 5,447,527 A | 9/1995 | Waldman | 607/88 |
| 5,503,637 A | 4/1996 | Kyricos | 607/88 |
| 5,592,153 A * | 1/1997 | Welling et al. | 340/825.19 |
| 5,620,247 A | 4/1997 | Swanson | 362/250 |
| 5,637,964 A * | 6/1997 | Hakkarainen et al. | 315/295 |
| 5,733,032 A | 3/1998 | Bolta et al. | 362/97 |
| 5,824,024 A | 10/1998 | Dial | 607/88 |
| 6,398,384 B1 | 6/2002 | Siminovitch et al. | 362/225 |
| 6,481,688 B1 * | 11/2002 | Welling et al. | 248/694 |
| 2004/0062048 A1 | 4/2004 | Eusterbrock | 362/411 |

FOREIGN PATENT DOCUMENTS

| | | |
|---|---|---|
| CA | 1334399 | 2/1995 |
| FR | 2 550 043 | 2/1985 |
| GB | 2 156 960 A | 10/1985 |

* cited by examiner

*Primary Examiner*—Trinh V. Dinh
*Assistant Examiner*—Jimmy Vu
(74) *Attorney, Agent, or Firm*—Richard C. Litman

(57) ABSTRACT

A dimmable flex arm lamp for effecting task lamp functions and/or light therapy treatments. The dimmable flex arm lamp includes a base member configured to provide stabilized support for the lamp, a light holding member, a fluorescent full spectrum light removably mounted in the light holding member, a stem with a flexible portion longitudinally extending from the base member, an end of the stem being interconnected with the base, and an end of the flexible portion being interconnected with the light holding member. The dimmable flex arm lamp also includes a dimming control and is configured to effect task lamp functions and/or light therapy treatments.

15 Claims, 5 Drawing Sheets

DIMMABLE FLEX ARM LAMP

CROSS REFERENCE TO RELATED APPLICATIONS

This application claims priority to provisional application Ser. No. 60/465,100, filed Apr. 24, 2003, which is incorporated herein by reference.

BACKGROUND OF THE INVENTION

1. Field of the Invention

The present invention generally relates to fluorescent lights and, more particularly, to a dimmable flex arm lamp for effecting task lamp functions and/or light therapy treatments.

2. Description of the Related Art

It has long been known that particular levels of light attribute to health and psychological benefits. Although both ocular as well as non-ocular techniques have been employed in an attempt to achieve various such effects, ocular treatment appears to be most efficacious. Not only are the eyes highly specialized organs specifically adapted for sensing light, but a sizable portion of the brain is exclusively devoted to processing data generated by the retinas. Moreover, neurologists and anatomists have relatively recently demonstrated the existence of nerve pathways extending from the retinas that are separate and apart from the pathways linked to the sight center of the brain.

An example of an organ whose regulatory function is responsive to light sensed by the eyes is the pineal gland which secretes the hormone melatonin. The hormone is released during periods of darkness while production is abruptly halted when the eyes perceive bright light. Melatonin is distributed throughout the body via the blood and cerebrospinal fluid and can effect the function of organs by which it is metabolized to thereby influence sleep cycles, feeding cycles, reproduction cycles and other biological rhythms. It has therefore been suggested that phototherapy may effectively be employed to correct a melatonin imbalance which may have resulted from, for example, shift work, jet lag or life in the Polar Regions, and thereby remedy the accompanying symptoms.

Millions of north Americans feel the effects of malillumination which causes poor work conditions and can result in less energy and productiveness. Poor lighting environments can cause increased depression and even result in more severe cases called Seasonal Affective Disorder (SAD). This problem increases more and more as the winter months bring shorter and shorter days. Sunlight starvation also effects millions more in the form of a milder form called Winter Blues.

Simulated full spectrum light is color corrected light that operates in the range of 400 to 800 nanometers. This light simulates the optical brilliance of outdoor light at noontime. This light can be measured by two numbers, the Color Rendering Index (CRI) and the Kelvin Temperature or (Degrees Kelvin). The secret to true color light and optically balanced light is how close you can get to the optics of natural light. The sun at noon has a natural color temperature of 100 CRI and between 5000 and 5500 degrees Kelvin. Both CRI and Kelvin are important for the simulation sunlight.

When light is simulated that matches the optical brilliance of sunlight pupils in one's eyes become smaller. This response generates clearer vision and higher perception. The results are lower glare and eye fatigue. When Lux intensity is combined with high CRI and balanced Kelvin temperature, quality light is obtained that not only matches the optical brilliance of the sun, but reduces levels of melatonin and the stress hormone, cortisol. Full spectrum light is not blue light or daylight color. It is clear, brilliant, white light and simulates the exact color of sunlight at noon. Many people currently progress through life missing sunlight because of the enormous amounts of time that are spent indoors. A need exists for conveniently providing individuals with simulated full spectrum light to enable them to receive brilliant life giving wave lengths which are much more effective in treating seasonal depression than any other source or color of light.

The related art is represented by the following references of interest.

U.S. Patent Application Publication No. 2004/0062048 A1, published on Apr. 1, 2004 for Paul Eusterbrock, describes a floor lamp which includes a dimmer switch at a mid-point of the main supporting post in order to allow maximum accessibility for the users. The Eusterbrock application does not suggest a dimmable flex arm lamp according to the claimed invention.

U.S. Pat. No. 5,047,006, issued on Sep. 10, 1991 to Howard Brandston, describes a personal integrating sphere system that provides a field of illumination of substantially uniform intensity for beneficially affecting the mental and physical health of a user. The Brandston patent does not suggest a dimmable flex arm lamp according to the claimed invention.

U.S. Pat. No. 5,426,879, issued on Jun. 27, 1995 to Irv Hecker, describes a natural daylight window simulation unit. The Hecker patent does not suggest a dimmable flex arm lamp according to the claimed invention.

U.S. Pat. No. 5,447,527, issued on Sep. 5, 1995 to Murray M. Waldman, describes a therapeutic method of using a lamp with a fixture for retaining a light bulb in a position to be viewed by the eyes of a patient, apparatus for restricting the wavelengths of light emitted by the light bulb to those between 490 and 520 nanometers, and apparatus for restricting the light energy irradiance to between about 1.8 and 200 microwatts per square centimeter over at least the eyes of the patient. The Waldman patent does not suggest a dimmable flex arm lamp according to the claimed invention.

U.S. Pat. No. 5,503,637, issued on Apr. 2, 1996 to Christopher J. Kyricos et al., describes an apparatus for producing and delivering high-intensity light to the eyes of a subject to modify the subject's circadian phase. The Kyricos et al. patent does not suggest a dimmable flex arm lamp according to the claimed invention.

U.S. Pat. No. 5,620,247, issued on Apr. 15, 1997 to Dennis K. Swanson, describes a stand-alone electric lamp that includes a base and a general area light source affixed to an opposite end of one of a pair of stems to provide general area lighting. The Swanson patent does not suggest a dimmable flex arm lamp according to the claimed invention.

U.S. Pat. No. 5,733,032, issued on Mar. 31, 1998 to Charles J. Bolta et al., describes a mobile light panel stand that supports a light panel suited to treat humans who are in need of exposure to light in a manner known as light therapy. The Bolta et al. patent does not suggest a dimmable flex arm lamp according to the claimed invention.

U.S. Pat. No. 5,824,024, issued on Oct. 20, 1998 to Daniel C. Dial, describes illumination fixtures for use in treating light deficiency and mood disorders, as well as color therapy. The Dial patent does not suggest a dimmable flex arm lamp according to the claimed invention.

U.S. Pat. No. 6,488,698 B1, issued on Dec. 3, 2002 to Henry H. Hyman, describes a portable light unit for treatment of seasonal affective disorders. The Hyman patent does not suggest a dimmable flex arm lamp according to the claimed invention.

U.S. Pat. No. 6,669,627 B1, issued on Dec. 30, 2003 to Scott S. Campbell et al., describes devices for exposing an extraocular region of a human to light during sleep which enhances REM sleep. The Campbell et al. patent does not suggest a dimmable flex arm lamp according to the claimed invention.

France Patent Application Publication No. 2,550,043 A1, published on Feb. 1, 1985, describes a ballast circuit with an illumination level control. The France '043 application does not suggest a dimmable flex arm lamp according to the claimed invention.

Great Britain Patent Application Publication No. 2,156,960 A, published on Oct. 16, 1985, describes a work table lamp with an arm having an upstanding portion and parallel branches. The Great Britain '960 application does not suggest a dimmable flex arm lamp according to the claimed invention.

Canada Patent No. 1,334,399, published on Feb. 14, 1995, describes a therapeutic lamp. The Canada '399 patent does not suggest a dimmable flex arm lamp according to the claimed invention.

None of the above inventions and patents, taken either singly or in combination, is seen to describe the instant invention as claimed. Thus a dimmable flex arm lamp solving the aforementioned problems is desired.

SUMMARY OF THE INVENTION

The present invention is a dimmable flex arm lamp for effecting task lamp functions and/or light therapy treatments. The dimmable flex arm lamp includes a base member configured to provide stabilized support for the lamp, a light holding member; a fluorescent full spectrum light removably mounted in the light holding member, a stem with a flexible portion longitudinally extending from the base member, an end of the stem being interconnected with the base, and an end of the flexible portion being interconnected with the light holding member. The dimmable flex arm lamp also includes a dimming control and is configured to effect task lamp functions and/or light therapy treatments.

The dimmable flex arm lamp may be configured as a desk lamp or a floor lamp. The base member may also include a clamp. The fluorescent full spectrum light may be a tri-phosphor fluorescent light that is color corrected light that operates in the range of 400 to 800 nanometers, and that simulates the optical brilliance of outdoor light at noontime. The fluorescent full spectrum light provides optical performance of up to about 91 Color Rendering Index and 5500 Kelvin. The fluorescent full spectrum light provides up to about 10,000 Lux for effecting light therapy treatments. The light therapy treatments may include depression, Seasonal Affective Disorder, stress, learning disabilities, pre-menstral syndrome dysfunctions, visual disorders, immune and nervous system abnormalities, sleep and other natural rhythm disorders.

An additional fluorescent full spectrum light may be interconnected on top of the light holding member, the additional fluorescent full spectrum light enabling a user to utilize one full spectrum light as a task light while simultaneously using the other full spectrum light to treat a light therapy condition. The dimmable flex arm lamp may also include a power on/off switch/control with switch means for turning the fluorescent full spectrum light on and off. The power on/off switch/control may be mounted within the base member or in the stem. The switch/control may be a knob or dial rotatable in one direction to turn the lamp on, and rotatable in another direction to turn the lamp off, or may be a push button control. The dimming control may be a phase control dimmer.

The dimmable flex arm lamp also includes an electronic ballast configured with instant start circuitry, rapid start circuitry, or programmed start circuitry, or an electromagnetic ballast configured with instant start circuitry, rapid start circuitry, or preheat start circuitry. The dimmable flex arm lamp may also include an internal power supply.

Accordingly, it is a principal aspect of the invention to provide a dimmable flex arm lamp including a base member configured to provide stabilized support for the lamp, a light holding member, a fluorescent full spectrum light removably mounted in the light holding member, a stem with a flexible portion longitudinally extending from the base member, an end of the stem being interconnected with the base, and an end of the flexible portion being interconnected with the light holding member. The dimmable flex arm lamp also includes a dimming control and is configured to effect task lamp functions and/or light therapy treatments.

It is an aspect of the invention to provide improved elements and arrangements thereof in a dimmable flex arm lamp for the purposes described which is inexpensive, dependable and fully effective in accomplishing its intended purposes.

These and other aspects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
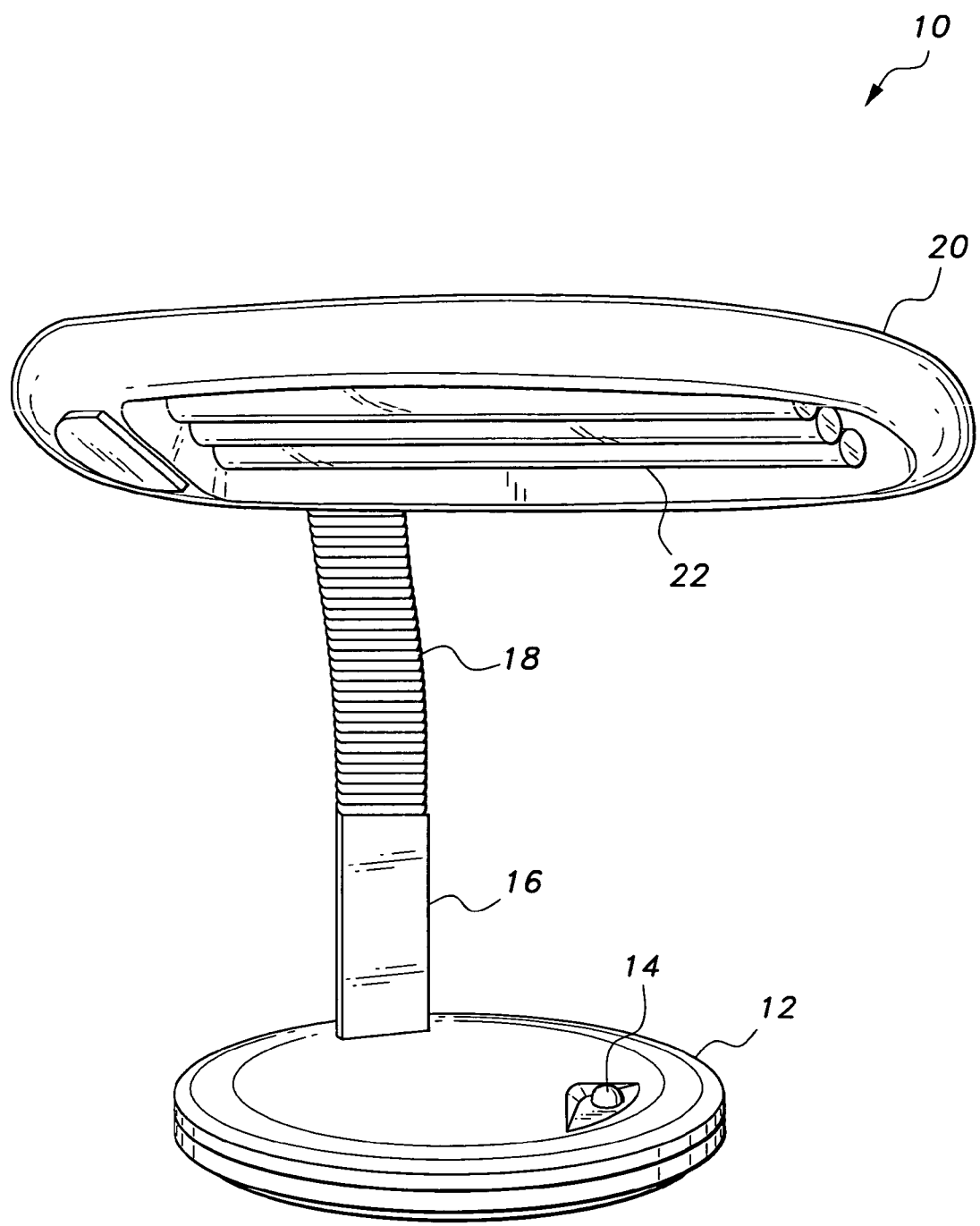
FIG. 1 is a front perspective view of an example of a dimmable flex arm lamp according to the present invention.

The present invention is a dimmable flex, arm lamp for effecting task lamp functions and/or light therapy treatments. The invention disclosed herein is, of course, susceptible of embodiment in many different forms. Shown in the drawings and described herein below in detail are preferred embodiments of the invention. It is to be understood, however, that the present disclosure is an exemplification of the principles of the invention and does not limit the invention to the illustrated embodiments.

Referring to the drawings, FIG. 1 shows one example of a dimmable flex arm lamp 10 according to the invention. The lamp 10 may be placed on a table, desk, or the like, and includes a base member 12 that provides stabilized support for the lamp 10. A power on/off switch/control 14 is mounted within the base member 12. A neck or stem 16 with a flexible portion 18 longitudinally extends from the base member 12 for a predetermined distance. An end of the neck or stem 16 is interconnected with the base 12, and an end of the flexible portion 18 is interconnected with a light holding member 20.

A fluorescent full spectrum light 22 is removably mounted in the light holding member 20. As used herein full spectrum light is color corrected light that operates in the range of 400 to 800 nanometers, and that simulates the optical brilliance of outdoor light at noontime. The lamp 10 also includes a dimming control, a ballast, and a light feedback control, and may be externally and/or internally powered by a power supply. The elements of the lamp 10 may be formed of any from any heat stable, lightweight, rigid, and durable material which allows the component parts of the lamp 10 to be securingly affixed thereto.

The flexible portion 18 enables the light holding member 20 to be readily adjusted so as to enable a user to adjust the light holding member 20 so the lamp 10 can effect task lamp functions, and to adjust the light holding member 20 so the lamp 10 can effect light therapy treatments. Light therapy treatments, as used herein, may be used for conditions including depression, SAD, stress, learning disabilities, premenstral syndrome dysfunctions, visual disorders, immune and nervous system abnormalities, sleep and other natural rhythm disorders, and other types of conditions.

Figure 2:
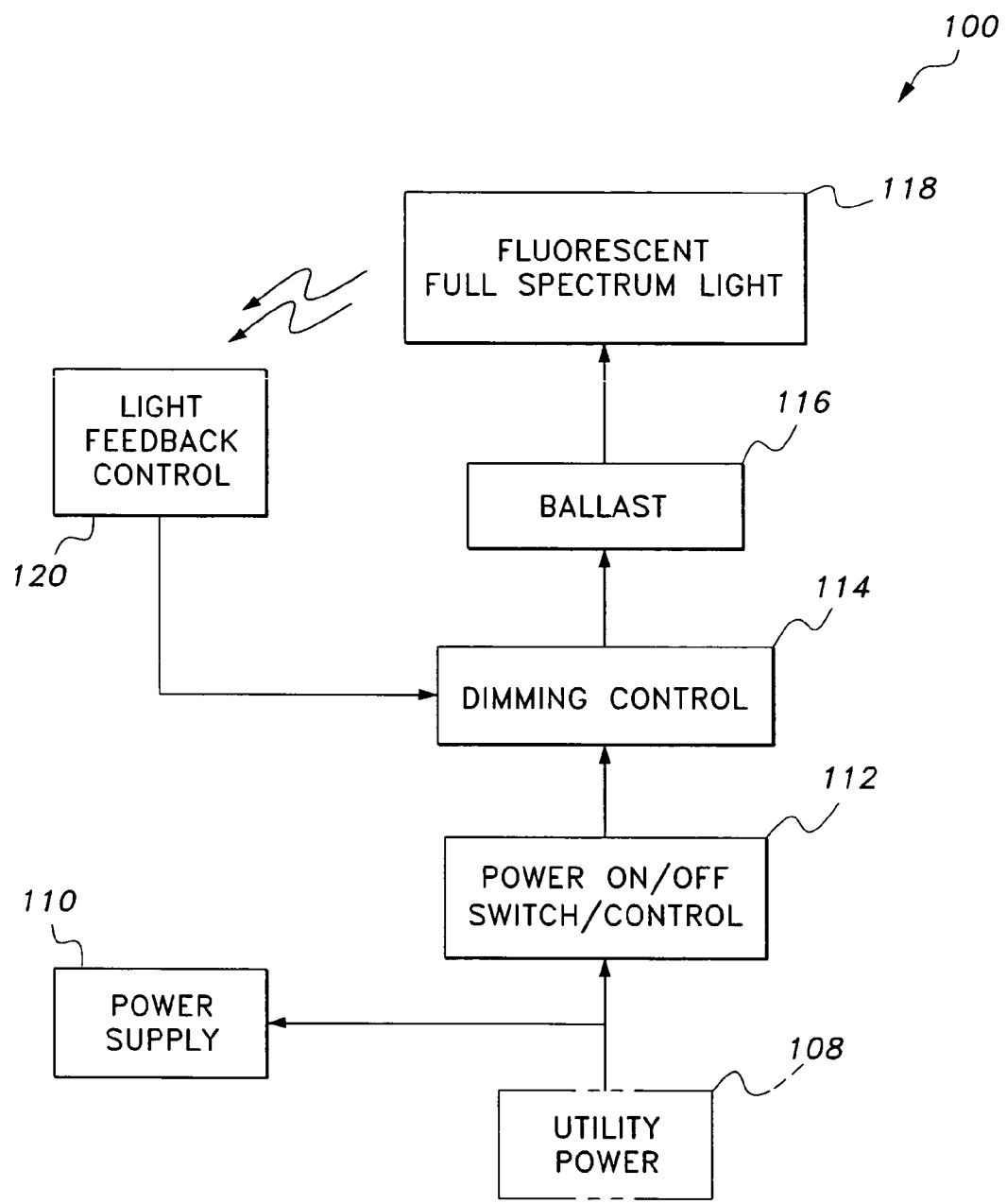
FIG. 2 is a block diagram of the dimmable flex arm lamp shown in FIG. 1.

FIG. 2 illustrates circuitry 100 for the lamp 10 shown in FIG. 1. External power, e.g. utility power 108, is provided to the power on/off switch/control 112. The lamp 10 may include a rechargeable and/or non-rechargeable power supply 110 so the lamp 10 may be used when the external utility power 108 becomes disconnected or is otherwise unavailable. A dimming control 114 is interconnected with the power on/off switch/control 112 and provides power to the ballast 116 which powers the fluorescent full spectrum light 118. Illumination emitted from the light 118 is detected by a light feedback control 120 and provides feedback signals to the dimming control 114.

The utility power 108 may be conventional 60 Hz AC line power, although any type of external power source may be utilized. The lamp 10 may include an internal power supply 110 which may be a rechargeable and/or non-rechargeable battery. When the lamp includes such a power supply 110, the power supply also includes a power inverter to convert the DC power to high frequency AC power.

The power on/off switch/control 112 is mounted within the base member 12. The switch/control 112 may be configured in the form of appropriate switch means for turning the light 118 on and off. For example, the switch/control 112 may a knob or dial rotatable in one direction to turn the lamp on, e.g. clockwise, and rotatable in the other direction to turn the lamp off, e.g. counterclockwise. Rotation of such a knob or dial may also cause the dimming control 114 to dim the light 118 to a brighter intensity or to a darker intensity according to the way the knob is turned.

The switch/control 112 may alternatively be configured as a one and/or two push button control and may be used alternately or simultaneously. One push button operation may be effected by configuring the switch/control 112 with one button, and pressing the switch/control 112 button briefly, e.g., below a predetermined period of time, to switch the lamp 10 on or off. By pressing the switch/control 112 button longer, e.g., above the predetermined period of time, the lamp 10 dims alternately up or down. The last brightness level may be stored in the lamp 10 when the lamp 10 is switched off, and may be retrieved when the lamp 10 is switched on.

Two push button operation may effected by configuring the switch/control 112 with a BRIGHTER button and a DARKER button. By pressing the switch/control 112 BRIGHTER button briefly, e.g., below a predetermined period of time, the lamp 10 is switched on or off. By pressing the switch/control 112 BRIGHTER button longer, e.g., above the predetermined period of time, the lamp 10 dims brighter up to a maximum level. By pressing the DARKER button briefly, e.g. below a predetermined period of time, the lamp 10 switches off. By pressing the switch/control 112 DARKER button longer, e.g. above the predetermined period of time, the lamp 10 dims darker down to a minimum level. The last brightness level may be stored in the lamp 10 when the lamp 10 is switched off, and may be retrieved when the lamp 10 is switched on. Other types of switch means known in the art may be provided as the switch/control 112, such as pivot switches or the like, and may be manually operated or electronically controlled devices.

The dimming control 114 may be a phase control dimmer that operates by periodically blocking the supply voltage to the full spectrum light 118 in accordance with a phase delay during each half cycle of an AC applied voltage. Such a phase control dimmer may utilize a thyristor, such as a silicon controlled rectifier or, more commonly, a triac as an electronic blocking device or switch. Gate turn off devices, and bipolar and MOSFET transistors may also be used in such a phase control dimmer.

A triac typically includes a cathode, an anode, and a gate (or control terminal). Current may be injected into or drawn out of the gate to make the triac bi-directionally conductive, e.g., to fire the triac. Once fired, the triac will remain conductive until the current through it drops below a certain level known as the holding current. By firing the triac at some adjustable phase delay after each zero crossing of the applied voltage (generally sinusoidal), one can vary the brightness of the full spectrum light 118.

The ballast 116 is preferably an electronic ballast but may, alternatively, be an electromagnetic ballast. An electronic ballast operates at about 20,000 Hz and is more efficient than an electromagnetic ballast which operates at about 60 Hz. An electronic ballast lacks the core and coil found in an electromagnetic ballast, and utilizes small magnetic devices and electric components to convert 60 Hertz line frequency to the 20,000 Hertz output frequency needed to power the full spectrum fluorescent light 118. The ballast 116 may be configured to operate with universal voltage inputs having input voltage ranging from about 85 volts to about 277 volts, and may also be configured to operate with induction lamps.

The ballast 116 may be configured with instant start circuitry, rapid start circuitry, programmed start circuitry, or preheat start circuitry. Instant start circuitry may be used when the ballast 116 is either an electronic or an electromagnetic ballast. Instant start circuitry produces light almost instantly.

Rapid start circuitry may also be used if the ballast 116 is either electronic or electromagnetic. When the ballast 116 is configured with rapid start circuitry, the fixture in the ballast 116 should be properly grounded and the full spectrum fluorescent light 118 positioned with proper spacing from the fixture, such one inch or lower. A momentary delay of less than about two seconds may be experienced when the lamp 10 is activated using the switch/control 112. When the ballast 116 is configured with rapid start circuitry continuous lamp filament heating is provided after the lamp 10 is started to optimize the life of the full spectrum light 118. If the electrode filaments of the full spectrum light 118 are not continuously heated when the ballast 116 is configured with rapid start circuitry, the filaments of the full spectrum light 118 may deteriorate prematurely, and the life of the light 118 will be shortened.

Programmed start lighting circuitry may be used when the ballast 116 is configured as an electronic ballast. With programmed lighting circuitry, the lamp 10 starting is similar to the rapid start circuitry, but is improved for frequent lamp starting applications, such as when the lamp 10 is occupancy sensor controlled. Programmed lighting circuitry provides precise controlled pre-heat of the filaments of the light 118 before the starting voltage is applied. Filament stress and depletion of filament emissive material is minimized with programmed lighting circuitry during the starting phase of the lamp 100, and results in maximum life of the full spectrum light 118.

Preheat circuitry may be used when the ballast 116 is configured as an electromagnetic ballast. With preheat circuitry, a separate starting switch in series with the lamp 10 and external to the magnetic ballast may be used to help start the lamp. With preheat circuitry, the electrodes of the full spectrum light 118 require a few seconds to attain a proper operating temperature for starting, and there is a delay in producing light.

The ballast 116 provides the proper voltage to establish an arc between the two electrodes, regulates the electric current flowing through the lamp 10 to stabilize light output, and supplies the correct operating voltage to provide a predetermined amount of operating current for the lamp 10. The ballast 116 may also be configured to compensate for supply voltage variations.

The fluorescent full spectrum light 22 is removably mounted in the light holding member 20. The full spectrum light 22 operates cooler than an incandescent light, and converts electrical energy to light more efficiently. The full spectrum light 22 relies upon an electrical arc passing between two electrodes, one on each end of the full spectrum light 22. This arc is conducted through a glass tube coated with phosphor by a mixture of vaporized mercury and purified gases (e.g., mainly Argon or Krypton). The resulting ultra-violet waves react with the phosphor to produce a glow and emit a full spectrum fluorescent light.

The full spectrum light 118 may be a tri-phosphor fluorescent light, may be configured with solderless pins to prolong lamp life by eliminating a common cause of failure, an alignment notch to insure proper installation for the best performance, a cathode guard to keep the light 118 burning brighter and longer by reducing end burning, a mercury capsule that has 43% less mercury than the industry standard, and a tri-phosphor blend to provide full spectrum white light with superior color rendering.

The CRI refers to color rendition and, specifically, how the color of an object appears under the artificial light source illuminating as compared to natural outdoor sunlight. Color temperature refers to the quality of light emanating from the artificial light source and is represented by the number of degrees Kelvin based on the Kelvin color temperature scale. The color temperature of outside light varies from 5000K to 5500K depending on the time of day, weather, season and latitude. The higher the color of a fluorescent lamp, the bluer (cooler) the appearance. The lower the color temperature the redder (warmer) it's appearance.

The CRI and the color temperature are independent of each other. Two different lamps may have the same color temperature and yet have a different CRI. The lamp with the highest color rendering index will generally have the lower initial lumen output of the two.

The full spectrum light 118 uses naturally balanced full spectrum light that simulates the sun's visible wavelengths and brings clear, glare free light indoors. The lamp 10 is as bright as a 300 watt halogen bulb, and can be used as a fully functional task lamp for reading, artwork, sewing and any type of other work station application. The light 118 provides optical performance of about 91+CRI and 5500 Kelvin, and also provides up to about 10,000 Lux for effecting light therapy treatments, such as SAD, winter depression, etc. The full spectrum light 118 is fully dimmable from 100% to 10% for maximum comfort.

Figure 3:
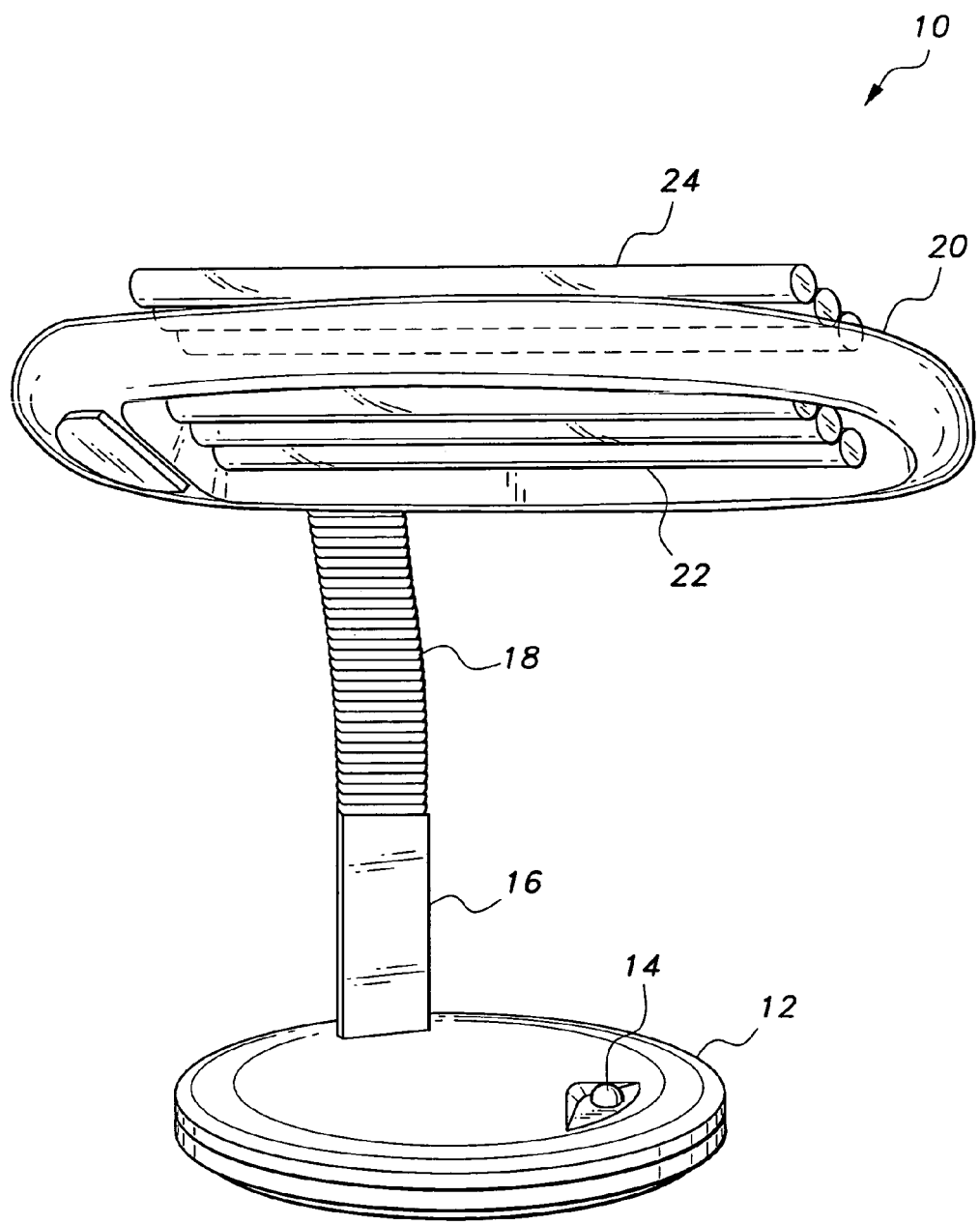
FIG. 3 is a front perspective view of another example of a dimmable flex arm lamp according to the present invention.

FIG. 3 illustrates another dimmable flex arm lamp 10 that is similar to the lamp shown in FIG. 1. As in FIG. 1, the lamp 10 is configured to be placed on a table, desk, or the like, and includes a base member 12 that provides stabilized support for the lamp 10. A power on/off switch/control 14 is mounted within the base member 12. A neck or stem 16 with a flexible portion 18 longitudinally extends from the base member 12 for a predetermined distance. An end of the neck or stem 16 is interconnected with the base 12, and an end of the flexible portion 18 is interconnected with a light holding member 20.

A fluorescent full spectrum light 22 is removably mounted in the light holding member 20. The lamp 10 also includes a dimming control, a ballast, and a light feedback control, and may be externally and/or internally powered by a power supply. The elements of the lamp 10 may be formed of any from any heat stable, lightweight, rigid, and durable material which allows the component parts of the lamp 10 to be securingly affixed thereto. All of these elements are as described above for the lamp 10 shown in FIG. 1.

The lamp 10 shown in FIG. 3, however, also includes an additional full spectrum light 24 interconnected on the top of the light holding member 20, as well as an additional ballast and dimming control for the additional full spectrum light 24. The full spectrum light 24 enables a user to utilize the full spectrum light 22 of the lamp 10 of FIG. 3 as a task light while simultaneously using the light 24 of the lamp 10 of FIG. 3 to treat light therapy conditions, such as SAD, winter depression, etc. Alternatively, the full spectrum light 22 enables a user to utilize the full spectrum light 24 of the lamp 10 of FIG. 3 as a task light while simultaneously using the light 22 of the lamp 10 of FIG. 3 to treat light therapy conditions, such as SAD, winter depression, etc.

Figure 4:
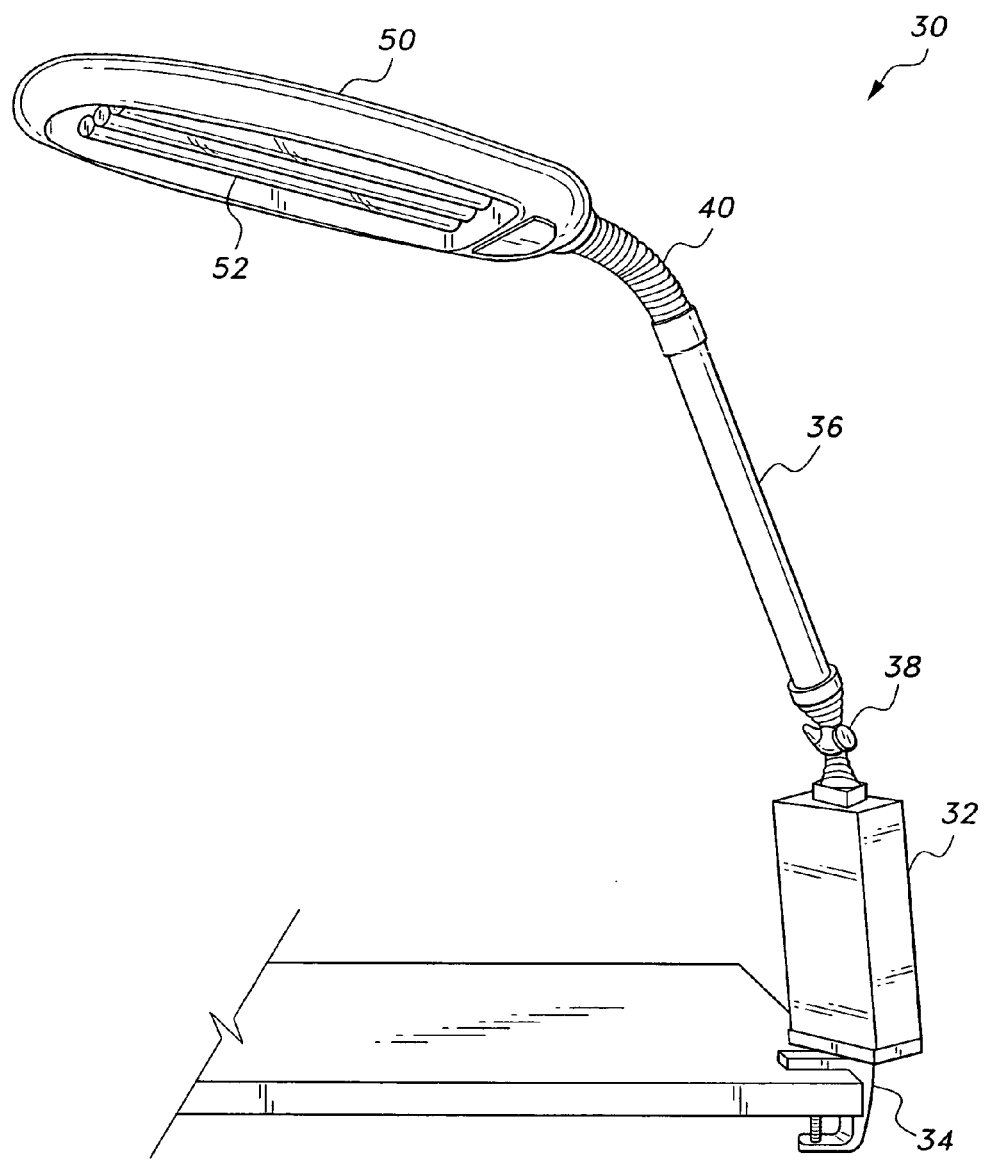
FIG. 4 is a front perspective view of another example of a dimmable flex arm lamp according to the present invention.

FIG. 4 illustrates another example of a dimmable flex arm lamp 30 according to the invention. The lamp 30 is configured to be removably mounted on a table, desk, or the like, and includes a base member 32 that provides stabilized support for the lamp 30 to a mounting surface via a clamp 34. A power on/off switch/control 38 is mounted within the base member 12. A neck or stem 36 with a flexible portion 40 longitudinally is pivotally interconnected with the base member 32 via a pivotal connection and extends longitudinally for a predetermined distance. An end of the neck or stem 36 is pivotally interconnected with the base 12, and an end of the flexible portion 40 is interconnected with a light holding member 50.

A fluorescent full spectrum light 52 is removably mounted in the light holding member 50. The full spectrum light 52 enables a user to utilize the full spectrum light 52 of the lamp 30 as a task light or to treat light therapy conditions, such as SAD, winter depression, etc. The lamp 50 also includes a dimming control, a ballast, and a light feedback control, and may be externally and/or internally powered by a power supply. The elements of the lamp 50 may be formed of any from any heat stable, lightweight, rigid, and durable material which allows the component parts of the lamp 50 to be securingly affixed thereto. All of these elements are as described above for the lamp 10 shown in FIG. 1.

Figure 5:
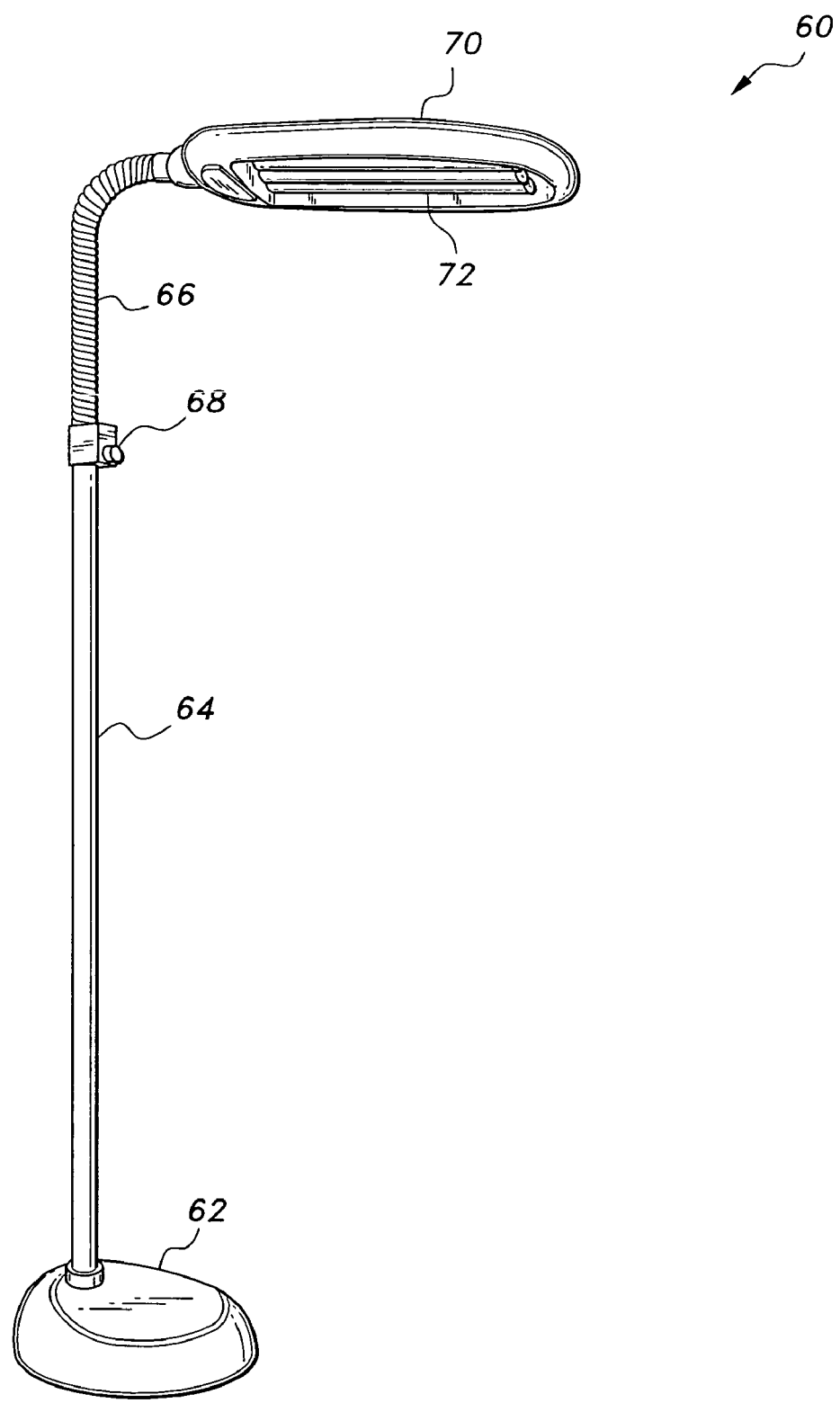
FIG. 5 is a front perspective view of another example of a dimmable flex arm lamp according to the present invention.

FIG. 5 illustrates another example of a dimmable flex arm lamp 60 according to the invention. The lamp 60 is configured as a floor lamp and includes a base member 62 that provides stabilized support for the lamp 60 to a floor surface. A neck or stem 64 with a flexible portion 66 longitudinally extends from the base member 62 for a predetermined distance. An end of the neck or stem 64 is interconnected with the base 62, and an end of the flexible portion 66 is interconnected with a light holding member 70.

A fluorescent full spectrum light 72 is removably mounted in the light holding member 70. The full spectrum light 72 enables a user to utilize the full spectrum light 72 of the lamp 60 as a task light or to treat light therapy conditions, such as SAD, winter depression, etc. The lamp 60 also includes a dimming control, a ballast, and a light feedback control, and may be externally and/or internally powered by a power supply. The elements of the lamp 60 may be formed of any from any heat stable, lightweight, rigid, and durable material which allows the component parts of the lamp 60 to be securingly affixed thereto. All of these elements are as described above for the lamp 10 shown in FIG. 1.

A dimmable flex arm lamp according to the invention may be configured in a variety of ways without departing from the scope of the disclosed flex arm lamp examples. For example, the dimmable flex arm lamp according to the invention may be configured as a dimmable full spectrum floor lamp for treating light therapy conditions, a dimmable full spectrum desk task lamp and light therapy unit, a dimmable natural light floor task lamp and light therapy unit, a natural light desk task lamp and light therapy unit, a flexible armed task device and light therapy unit, a dimmable flex arm task lamp and SAD therapy unit, a 10,000 Lux flex arm task lamp and light therapy unit, a high output full spectrum task lamp and light therapy unit. The dimmable flex arm lamp may also be configured with 36 or 65 watt fluorescent full spectrum lights.

The dimmable flex arm lamp according to the invention may also be configured to operate with a variety of fluorescent full spectrum lights configured to operate at various wattage levels, such as anywhere between about 5 watts to about 250 watts. For example, the dimmable flex arm lamp according to the invention may be configured as a 55 watt 91 CRI 5500 Kelvin task lamp and light therapy unit, a 55 watt floor task lamp and light therapy unit, a 55 watt dimmable full spectrum task lamp and light therapy unit, a 55 watt full spectrum floor task lamp and light therapy unit, a 27 watt dimmable full spectrum task lamp and light therapy unit, a 27 watt dimmable natural daylight task lamp and light therapy unit, and a 27 watt full spectrum task lamp and light therapy unit.

While the invention has been described with references to its preferred embodiment, it will be understood by those skilled in the art that various changes may be made and equivalents may be substituted for elements thereof without departing from the true spirit and scope of the invention. In addition, many modifications may be made to adapt a particular situation or material to the teaching of the invention without departing from its essential teachings.

I claim:

1. A dimmable flex arm lamp comprising:
   a base member configured to provide stabilized support for the lamp;
   a light holding member;
   a fluorescent full spectrum light removably mounted in the light holding member;
   a stem with a flexible portion longitudinally extending from the base member, an end of the stem being interconnected with the base, and an end of the flexible portion being interconnected with the light holding member;
   a dimming control; and
   a power on/off switch/control including switch means for turning the fluorescent full spectrum light on and off;
   wherein said dimmable flex arm lamp is configured to effect task lamp functions and light therapy treatments.

2. The dimmable flex arm lamp according to claim 1, wherein said lamp is configured as a desk lamp or a floor lamp.

3. The dimmable flex arm lamp according to claim 1, wherein the base member further comprises a clamp.

4. A dimmable flex arm lamp comprising:
   a base member configured to provide stabilized support for the lamp;
   a light holding member;
   a fluorescent full spectrum light removably mounted in the light holding member, wherein said fluorescent full spectrum light is a tri-phosphor fluorescent light that is color corrected and operates in a range of 400 to 800 nanometers;
   a stem with a flexible portion longitudinally extending from the base member, an end of the stem being interconnected with the base, and an end of the flexible portion being interconnected with the light holding member; and
   a dimming control;
   wherein said dimmable flex arm lamp is configured to effect task lamp functions and light therapy treatments.

5. The dimmable flex arm lamp according to claim 4, wherein said fluorescent full spectrum light provides optical performance of up to about 91 Color Rendering Index and 5500 Kelvin.

6. The dimmable flex arm lamp according to claim 4, wherein said fluorescent full spectrum light provides up to about 10,000 Lux for effecting light therapy treatments.

7. The dimmable flex arm lamp according to claim 6, wherein said light therapy treatments include depression, Seasonal Affective Disorder, stress, learning disabilities, pre-menstral syndrome dysfunctions, visual disorders, immune and nervous system abnormalities, sleep and other natural rhythm disorders.

8. The dimmable flex arm lamp according to claim 1, further comprising an additional fluorescent full spectrum light interconnected on top of the light holding member, and an additional dimming control, said additional fluorescent full spectrum light enabling a user to utilize one fluorescent full spectrum light as a task light while simultaneously using the other fluorescent full spectrum light to treat a light therapy condition.

9. The dimmable flex arm lamp according to claim 1, wherein said power on/off switch/control is mounted within the base member.

10. The dimmable flex arm lamp according to claim 1, wherein said power on/off switch/control is mounted in the stem.

11. The dimmable flex arm lamp according to claim 1, wherein said switch means is a knob or dial rotatable in one direction to turn the lamp on, and rotatable in another direction to turn the lamp off.

12. The dimmable flex arm lamp according to claim 1, wherein said switch means is a push button control.

13. The dimmable flex arm lamp according to claim 1, wherein said dimming control comprises a phase control dimmer.

14. The dimmable flex arm lamp according to claim 1, further comprising an internal power supply.

15. A dimmable flex arm lamp comprising:
- a base member configured to provide stabilized support for the lamp;
- a light holding member;
- a fluorescent full spectrum light removably mounted in the light holding member;
- a stem with a flexible portion longitudinally extending from the base member, an end of the stem being interconnected with the base, and an end of the flexible portion being interconnected with the light holding member;
- a dimming control; and
- a ballast selected from the group consisting of an electronic ballast and an electromagnetic ballast, said ballast being configured with instant start circuitry, rapid start circuitry, or preheat start circuitry;
- wherein said dimmable flex arm lamp is configured to effect task lamp functions and light therapy treatments.

* * * * *